United States Patent [19]

Felder et al.

[11] Patent Number: 5,066,823
[45] Date of Patent: Nov. 19, 1991

[54] PREPARATION OF 5-ACYLAMINO-2,4,6-TRIIODO- OR TRIBROMO-BENZOIC ACID DERIVATIVES

[75] Inventors: Ernest Felder; Carlo Musu; Luciano Fumagalli; Fulvio Uggeri, all of Milan, Italy

[73] Assignee: Bracco Industria Chemica S.P.A., Milan, Italy

[21] Appl. No.: 424,216

[22] PCT Filed: May 20, 1988

[86] PCT No.: PCT/EP88/00453

§ 371 Date: Oct. 10, 1989

§ 102(e) Date: Oct. 10, 1989

[87] PCT Pub. No.: WO88/09328

PCT Pub. Date: Dec. 1, 1988

[30] Foreign Application Priority Data

May 22, 1987 [IT] Italy ................ 20647 A/87
May 10, 1988 [IT] Italy ................ 47935 A/88

[51] Int. Cl.$^5$ ............................ C07C 315/04
[52] U.S. Cl. .................................. 560/13; 560/9; 560/16; 560/25; 560/26; 560/27; 560/30; 560/37; 560/43; 560/44; 560/45; 560/47; 562/430; 562/432; 562/443; 562/444; 562/451; 562/457; 562/621; 564/153; 564/154; 564/156; 564/158
[58] Field of Search ............... 564/153, 154, 156, 158; 560/9, 13, 16, 25, 26, 27, 30, 37, 43, 44, 45, 47; 562/430, 432, 443, 444, 451, 457, 621

[56] References Cited

U.S. PATENT DOCUMENTS

| | | | |
|---|---|---|---|
| 3,660,464 | 5/1972 | Bernstein et al. | 562/432 |
| 3,701,771 | 10/1972 | Almen et al. | 564/153 |
| 3,910,989 | 10/1975 | Felder et al. | 560/30 |
| 3,939,204 | 2/1976 | Buttermann | 562/432 |
| 4,001,298 | 1/1977 | Gries et al. | 562/432 |
| 4,065,554 | 12/1977 | Tilly et al. | 560/37 |
| 4,132,731 | 1/1979 | Klieger et al. | 562/451 |
| 4,191,775 | 3/1980 | Glen | 564/170 |
| 4,264,572 | 4/1981 | Klieger et al. | 562/451 |
| 4,321,368 | 3/1982 | Hoey | 560/37 |
| 4,348,377 | 9/1982 | Felder et al. | 564/153 |
| 4,547,357 | 10/1985 | Pfeiffer et al. | 564/153 |
| 4,567,034 | 1/1986 | Charles et al. | 560/47 |

OTHER PUBLICATIONS

Truce, W. E. et al., "The Smiles and Related Rearrangements of Aromatic Systems", *Organic Reactions*, Chap. 2, vol. 18, pp. 99–215 (1970).

Bayles, R. et al., "The Smiles Rearrangement, etc.", *Synthesis*, Communications, Nos. 31 and 33 (1977).

"Smiles Rearrangement", The Merck Index, Tenth Edition, p. ONR–84, 1983.

*Primary Examiner*—Allen J. Robinson
*Assistant Examiner*—Susan P. Treanor
*Attorney, Agent, or Firm*—Bucknam and Archer

[57] ABSTRACT

A process for the preparation of 5-acylamino-2,4,6-triiodo or tribromo-benzoic acid derivatives of formula (I), wherein X is I or Br, R is H or a variously substituted alkyl, or a group of formula (II), wherein X has the above meanings; Y is hydroxy, alkoxy, hydroxyalkoxy, alkylamino or hydroxyalkylamino; Z may be the same as COY or it is hydroxylalkylaminocarbonyl provided that at least one of the two acyl or R groups is hydroxy-substituted, which process comprises the rearrangement of the corresponding 5-(alkylaminocarbonyl-alkoxy)-2,4,6-trioodo ro tribromo-benzoic acid derivatives, in the presence of bases.

12 Claims, No Drawings

PREPARATION OF 5-ACYLAMINO-2,4,6-TRIIODO- OR TRIBROMO-BENZOIC ACID DERIVATIVES

The invention relates to a new synthetic process, particularly suited for the preparation of 5-acylamino-2,4,6-triiodo or tribromo-benzoic acid derivatives of formula I

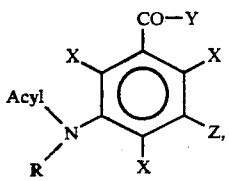

wherein:
X is I or Br,
Acyl is a $C_2$-$C_6$ hydroxyalkanoyl, alkoxyalkanoyl or alkoxy-hydroxyalkanoyl group or a $C_2$-$C_4$ unsubstituted alkanoyl group,
R is H or a $C_1$-$C_6$ alkyl, hydroxyalkyl, alkoxyalkyl or alkoxy-hydroxyalkyl group, or a $H(OCH_2CH_2)_{2-5}$—, $Me(OCH_2CH_2)_{2-4}$— or $Et(OCH_2CH_2)_{2-4}$— group, or a group of formula

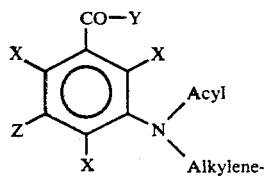

wherein X, Y, Z and Acyl have the same meanings as in formula I and
alkylene- is a straight or branched $C_2$-$C_8$ alkylene group, which in turn may be substituted by hydroxy groups and/or interrupted by O, S, SO or $SO_2$,
Y is a hydroxy, alkoxy, hydroxyalkoxy, alkylamino group or preferably a hydroxyalkylamino group of formula

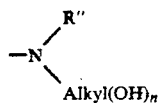

wherein R" is H or a $C_1$-$C_5$ alkyl, hydroxyalkyl, alkoxyalkyl or alkoxy-hydroxyalkyl group,
alkyl is a $C_2$-$C_5$ straight or branched alkyl group and n=1, 2 or 3,
Z may have the same meaning of CO—Y in formula I or may be a hydroxyalkylaminocarbonyl group of formula

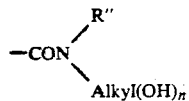

wherein R", Alkyl and n are as above defined or Z may also be a $C_2$-$C_5$ acylamino, hydroxyacylamino, N-alkyl-acylamino, N-hydroxyalkylacylamino or acylaminomethyl group,
with the proviso that at least one of the two Acyl or R groups is hydroxy substituted, said process being characterized in that corresponding 5-(alkylaminocarbonyl-alkoxy)-2,4,6-triiodo or tribromobenzoic acid derivatives of formula II, or 5-(acylamino-alkoxy)-2,4,6-triiodo or tribromo-benzoic acid derivatives of formula III,

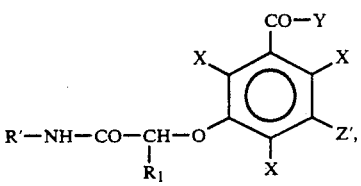

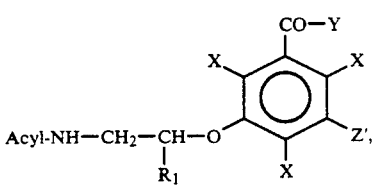

wherein:
X and Y have the same meanings as in formula I,
Z' may be the same as Z in formula I, but it may also be a group of formula

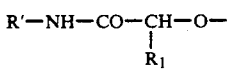

or

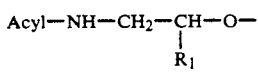

wherein R', $R_1$ and Acyl are as hereinbelow defined,
R' is H or a $C_1$-$C_6$ alkyl, hydroxyalkyl, alkoxyalkyl or alkoxy-hydroxyalkyl group or a $H(OCH_2CH_2)_{2-5}$—, $Me(OCH_2CH_2)_{2-4}$— or $Et(OCH_2CH_2)_{2-4}$— group, or a group of formula

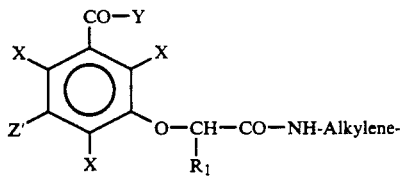

wherein X, Y, Z' are as above defined, $R_1$ is as hereinbelow defined, Alkylene- is a straight or branched $C_2$-$C_8$ alkylene group, which in turn may be substituted by hydroxy groups and/or interrupted by O, S, SO or $SO_2$,
$R_1$ is H or a $C_1$-$C_3$ alkyl, hydroxyalkyl or alkoxyalkyl group,
acyl is a $C_2$-$C_6$ hydroxyalkanoyl, alkoxyalkanoyl or alkoxy-hydroxyalkanoyl group or an unsubstituted $C_2$-$C_4$ alkanoyl group,
are subjected, in presence of bases, to a rearrangement reaction to give the desired compounds of formula I.

The present invention also relates to 5-acylamino-2,4,6-triiodo or tribromo-benzoic acid derivatives which, having never being disclosed so far, were for the first time obtained by the process described in the present invention.

Rearrangment reaction of II and/or respectively III into I is only formally analogous to Smiles rearrangement reaction (Smiles Rearrangement; The MERCK Index, Tenth Edition, Organic Name Reactions, pag. ONR-84) and may be represented as follows:

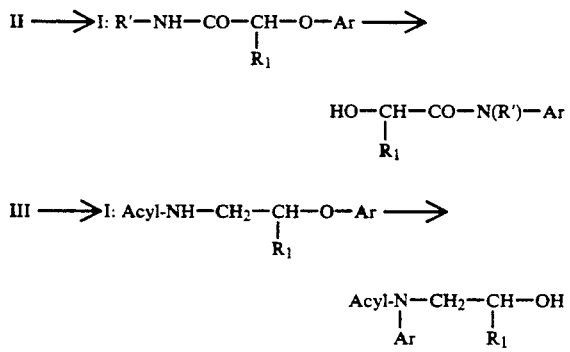

wherein:
R', $R_1$ and Acyl are as above defined and
Ar is a trihalo substituted aromatic ring as defined in formula I.

Rearrangement takes place in presence of bases and, generally but not exclusively, at a temperature equal to or higher than room temperature, in order to increase the reaction rate. The equilibrium which takes place between compound II or III and compound I is often so shifted towards I that, by means of the process described in the present invention, yields even higher than 90% may be obtained.

Said process is of the greatest interest from the technical point of view since it makes it possible to obtain compounds of formula I, starting from easily available compounds such as the ether derivatives of 5-hydroxy-2,4,6-triiodo or tribromo-benzoic acid, said compounds of formula I being very interesting but generally more difficult to obtain in high yields, according to the known methods.

Compounds of formula I are valuable components of contrast agents in radiology.

Among these, particularly, useful are some 5-(N-acyl-amino)-2,4,6-triiodo or tribromo-bis-(hydroxyalkyl-)isophthalamide derivatives, since they are non-ionic contrast agents endowed with good tolerability and high water-solubility. Ionic contrast agents used hitherto, are being replaced to a higher and higher extent by this new class of products, since it has a lot of outstanding advantages in particular as far as tolerability is concerned.

As in no way limitative examples of non-ionic contrast agents used in radiology, which may be prepared according to the process described in the present invention, the following compounds are hereinbelow reported;

Iopamidol=(S) N,N'-bis[2-hydroxy-1-(hydroxymethyl-)ethyl]-5-[(2-hydroxy-1-oxopropyl)amino]-2,4,6-triiodo-1,3-benzenedicarboxyamide; Ger. Pat. 2 547 789.

Iomeprol=N,N'-bis(2,3-dihydroxypropyl)-5-[(hydroxyacetyl)methylamino]-2,4,6-triiodo-1,3-benzenedicarboxyamide; Eur. Pat. 26 281.

Ioversol=N,N'-bis(2,3-dihydroxypropyl)-5-[(hydroxyacetyl)(2-hydroxyethyl)-amino]-2,4,6-triiodo-1,3-benzenedicarboxyamide; U.S. Pat. No. 4,396,598.

N,N'-bis[2-hydroxy-1-(hydroxymethyl)ethyl]-5-[(2-hydroxy-1-oxopropyl)methylamino]-2,4,6-triiodo-1,3-benzenedicarboxyamide; Eur. Pat. 26 281.

N,N'-bis[2-hydroxy-1-(hydroxymethyl)ethyl]-5-[(hydroxyacetyl)methylamino]-2,4,6-triiodo-1,3-benzenedicarboxyamide; Eur. Pat. 26 281.

1,3-bis[N-(3,5-bis-(2,3-dihydroxypropylaminocarbonyl)-2,4,6-triiodo-phenyl)-N-hydroxyacetyl-amino]propane; Eur. Pat. 23 992.

1,4-bis[N-(3,5-bis-(1,3-dihydroxyisopropylaminocarbonyl)-2,4,6-triiodo-phenyl)-N-hydroxyacetyl-amino]2,3-dihydroxybutane; Eur. Pat. 23 992.

The process of the invention also make it possible to prepare novel 5-acylamino-2,4,6-triiodo or tribromo-benzoic acid derivatives which are part of the disclosure and are useful contrast agents in radiology.

The search for novel aromatic tri- or hexa-iodine or bromine derivatives which are water-soluble, well tolerable, non-ionic and useful as radio-opaque agents is so difficult that the achievement of a product fullfilling even only one of such requirements must already be considered as inventive and accordingly patentable.

Examples of new compounds which fullfill the above said requirements, and which were obtained according to the process object of the present invention, are hereinbelow reported:

5-(N-2,3-dihydroxypropyl-N-hydroxyacetyl-amino)-2,4,6-triiodo-bis-(2,3-dihydroxypropyl)isophthalamide;

5-(N-2,3-dihydroxypropyl-N-hydroxyacetyl-amino)-2,4,6-triiodo-bis-(1,3-dihydroxyisopropyl)isophthalamide;

5-(N-2,3-dihydroxypropyl-N-α-hydroxypropionyl-amino)-2,4,6-triiodo-bis-(2,3-dihydroxypropyl)isophthalamide;

5-(N-2,3-dihydroxypropyl-N-α-hydroxypropionyl-amino)-2,4,6-triiodo-bis-(1,3-dihydroxyisopropyl)isophthalamide;

5-(N-1,3-dihydroxyisopropyl-N-hydroxyacetyl-amino)-2,4,6-tribromo-bis-(1,3-dihydroxyisopropyl)isophthalamide;

5-(N-1,3-dihydroxyisopropyl-N-hydroxyacetyl-amino)-2,4,6-triiodo-bis-(1,3-dihydroxyisopropyl)isophthalamide;

5-(N-2-hydroxyethyl-N-α-hydroxypropionyl-amino)-2,4,6-triiodo-bis-(2,3,4-trihydroxy-1-butyl)isophthalamide;

5-(N-2-hydroxyethyl-N-α-hydroxypropionyl-amino)-2,4,6-triiodo-bis-(1,3,4-trihydroxy-2-butyl)isophthalamide;

5-(N-2-hydroxy-3-methoxypropyl-N-hydroxyacetyl-amino)-2,4,6-triiodo-bis-(2,3-dihydroxypropyl)isophthalamide;

5-(N-methyl-N-hydroxyacetyl-amino)-2,4,6-triiodo-bis(2,3,4-trihydroxy-1-butyl)isophthalamide;

5-(N-methyl-N-hydroxyacetyl-amino)-2,4,6-triiodo-bis(1,3,4-trihydroxy-2-butyl)isophthalamide;

5-(N-2,3,4-trihydroxy-1-butyl-N-hydroxyacetil)-2,4,6-triiodo-bis(2-hydroxyethyl)isophthalamide;

5-(N-methyl-N-hydroxyacetyl-amino)-2,4,6-triiodo-((N-2,3-dihydroxypropyl)-(N'-2-hydroxyethyl)-)isophthalamide;

5-(N-2,3-dihydroxypropyl-N-hydroxyacetyl-amino)-2,4,6-triiodo-bis(2,3-dihydroxyethyl)isophthalate;

5-(N-methyl-N-hydroxyacetyl-amino)-2,4,6-triiodo-bis(1,3-dihydroxyisopropyl)isophthalate;

1,3-bis-(N-(3,5-bis(1,3-dihydroxyisopropylaminocarbonyl)-2,4,6-triiodo-phenyl)-N-hydroxyacetyl-amino)-2-hydroxypropane;

1,3-bis-(N-(3,5-bis(2,3-dihydroxypropylaminocarbonyl)-2,4,6-triiodo-phenyl)-N-hydroxyacetyl-amino)-2-hydroxypropane;

1,6-bis-(N-(3,5-bis(2,3-dihydroxypropylaminocarbonyl)-2,4,6-triiodo-phenyl)-N-hydroxyacetyl-amino)-2,3,4,5-tetrahydroxy-hexane;

1,7-bis-(N-(3,5-bis(1,3-dihydroxyisopropylaminocarbonyl)-2,4,6-triiodo-phenyl)-N-hydroxyacetyl-amino)-2,6-dihydroxy-4-oxa-heptane;

1,5-bis-(N-(3,5-bis(2,3-dihydroxypropylaminocarbonyl)-2,4,6-triiodo-phenyl)-N-hydroxyacetyl-amino)-3-thia-pentane;

1,5-bis-(N-(3,5-bis(2,3-dihydroxypropylaminocarbonyl)-2,4,6-triiodo-phenyl)-N-hydroxyacetyl-amino)-3-thia-pentane-3-oxide;

1,5-bis-(N-(3,5-bis(2,3-dihydroxypropylaminocarbonyl)-2,4,6-triiodo-phenyl)-N-hydroxyacetyl-amino)-3-thia-pentane-3,3-dioxide;

1,3-bis-(N-(3-(2,3-dihydroxypropylaminocarbonyl)-5-(2-hydroxyethylaminocarbonyl)-2,4,6-triiodo-phenyl)-N-hydroxyacetyl-amino)-2,2-bis-(hydroxymethyl)-propane;

1,3-bis-(N-(3-(1,3-dihydroxyisopropylaminocarbonyl)-5-(2-hydroxyethylaminocarbonyl)-2,4,6-triiodo-phenyl)-N-hydroxyacetyl-amino)-2,2-bis-(hydroxymethyl)-propane;

3,5-bis-(N-methyl-N-hydroxyacetyl-amino)-2,4,6-triiodo-(2,3-dihydroxypropyl)benzamide;

3,5-bis-(N-methyl-N-hydroxyacetyl-amino)-2,4,6-triiodo-(1,3-dihydroxyisopropyl)benzamide;

3,5-bis-(N-methyl-N-α-hydroxypropionyl-amino)-2,4,6-triiodo-(1,3-dihydroxyisopropyl)benzamide;

3,5-bis-(N-2-hydroxyethyl-N-hydroxyacetyl-amino)-2,4,6-triiodo-(2,3-dihydroxypropyl)benzamide;

3,5-bis-(N-2-hydroxyethyl-N-hydroxyacetyl-amino)-2,4,6-triiodo-(1,3-dihydroxyisopropyl)benzamide;

3,5-bis-(N-2-hydroxyethyl-N-α-hydroxypropionyl-amino)-2,4,6-triiodo-(2,3-dihydroxypropyl)benzamide;

3,5-bis-(N-2-hydroxyethyl-N-α-hydroxypropionyl-amino)-2,4,6-triiodo-(1,3-dihydroxyisopropyl)benzamide;

3,5-bis-(N-2-hydroxyethyl-N-hydroxyacetyl-amino)-2,4,6-triiodo-(2-hydroxyethyl)benzamide;

3,5-bis-(N-2-hydroxyethyl-N-hydroxyacetyl-amino)-2,4,6-triiodo-(N,N-bis-(2-hydroxyethyl))benzamide;

3,5-bis-(N-2-hydroxyethyl-N-hydroxyacetyl-amino)-2,4,6-triiodo-(2-hydroxyethyl)benzoate;

3,5-bis-(N-2-hydroxyethyl-N-hydroxyacetyl-amino)-2,4,6-triiodo-(2,3-dihydroxypropyl)benzoate;

3-(N-2-hydroxyethyl-N-hydroxyacetyl-amino)-5-acetylamino-2,4,6-triiodo-(2,3-dihydroxypropyl)benzamide;

3-(N-2-hydroxyethyl-N-hydroxyacetyl-amino)-5-(N-methyl-N-acetyl-amino)-2,4,6-triiodo-(2,3-dihydroxypropyl)benzamide;

3-(N-2-hydroxyethyl-N-hydroxyacetyl-amino)-5-acetylaminomethyl-2,4,6-triiodo-(2,3-dihydroxypropyl)benzamide;

3-(N-2-hydroxyethyl-N-hydroxyacetyl-amino)-5-acetylaminomethyl-2,4,6-triiodo-(2-hydroxyethyl)benzoate;

5-(N-2-hydroxyethyl-N-hydroxyacetyl-amino)-2,4,6-triiodo-bis-(N,N-bis(2-hydroxyethyl))isophthalamide;

5-(N-2,3-dihydroxypropyl-N-hydroxyacetyl-amino)-2,4,6-triiodo-bis-(N,N-bis(2-hydroxyethyl))isophthalamide;

5-(N-2-hydroxyethyl-N-α-hydroxypropionyl-amino)-2,4,6-triiodo-bis-(N,N-bis(2-hydroxyethyl))isophthalamide;

5-(N-2-hydroxyethyl-N-hydroxyacetyl-amino)-2,4,6-triiodo-bis-(N-2,3-dihydroxypropyl-N-2-hydroxyethyl)isophthalamide;

5-(N-2-hydroxyethyl-N-hydroxyacetyl-amino)-2,4,6-triiodo-bis-(N-1,3-dihydroxyisopropyl-N-2-hydroxyethyl)isophthalamide;

5-(N-methyl-N-hydroxyacetyl-amino)-2,4,6-triiodo-bis-(N-1,3-dihydroxyisopropyl-N-2-hydroxyethyl)isophthalamide;

1,3-bis-(N-(3,5-bis-(N,N-bis(2-hydroxyethyl)aminocarbonyl)-2,4,6-triiodo-phenyl)-N-hydroxyacetyl-amino)-2-hydroxy-propane;

1,3-bis-(N-(3,5-bis-(N,N-bis(2-hydroxyethyl)aminocarbonyl)-2,4,6-triiodo-phenyl)-N-hydroxyacetyl-amino)-propane;

1,3-bis-(N-(3,5-bis-(N,N-bis-(2-hydroxyethyl)aminocarbonyl)-2,4,6-triiodo-phenyl)-N-hydroxyacetyl-amino)-2,2-bis-(hydroxymethyl)-propane;

1,4-bis-(N-(3,5-bis-(N,N-bis(2-hydroxyethyl)aminocarbonyl)-2,4,6-triiodo-phenyl)-N-hydroxyacetyl-amino)-2,3-dihydroxy-butane;

1,4-bis-(N-(3,5-bis-(N,N-bis(2-hydroxyethyl)aminocarbonyl)-2,4,6-triiodo-phenyl)-N-α-hydroxypropionyl-amino)-2,3-dihydroxy-butane;

1,4-bis-(N-(3,5-bis-(N-1,3-dihydroxyisopropyl-N-2-hydroxyethyl-aminocarbonyl)-2,4,6-triiodo-phenyl)-N-hydroxyacetyl-amino)-2,3-dihydroxy-butane;

1,4-bis-(N-(3,5-bis-(N-1,3-dihydroxyisopropyl-N-2-hydroxyethyl-aminocarbonyl)-2,4,6-triiodo-phenyl)-N-α-hydroxypropionyl-amino)-2,3-dihydroxy-butane;

1,5-bis-(N-(3,5-bis-(N,N-bis(2-hydroxyethyl)aminocarbonyl)-2,4,6-triiodo-phenyl)-N-hydroxyacetyl-amino)-3-oxa-pentane;

1,5-bis-(N-(3,5-bis-(N,N-bis(2-hydroxyethyl)aminocarbonyl)-2,4,6-triiodo-phenyl)-N-hydroxyacetyl-amino)-3-thia-pentane.

In compounds of formula I, Acyl preferably is a 2-hydroxyalkanoyl group. Acyl-N(R)- in turn preferably represents a hydroxyacetylamino, α-hydroxypropionylamino, N-methyl-hydroxyacetylamino, L-N-methyl-α-hydroxypropionylamino, N-ethyl-hydroxyacetylamino, N-ethyl-α-hydroxypropionylamino, α-hydroxybutyrroylamino, N-methyl-α-hydroxybutyrroylamino, N-2-hydroxyethyl-hydroxyacetylamino, N-2,3-dihydroxypropyl-hydroxyacetylamino, N-1,3-dihydroxyisopropyl-hydroxyacetylamino-N-2-hydroxy-3-methoxypropyl-hydroxyacetylamino, N-2-hydroxy-3-ethoxypropyl-hydroxyacetylamino, N-2-methoxyethyl-hydroxyacetylamino, N-2-ethoxyethyl-hydroxyacetylamino, N-2-hydroxyethyl-α-hydroxypropionylamino, N-2-hydroxyethyl-N-α,β-dihydroxypropionylamino group.

Acyl may also be an unsubstituted or an alkoxysubstituted alkanoyl group, preferably an acetyl group, in such case R necessarily carrying a hydroxy group.

Some examples of possible substituents in 5-position are the following: N-2-hydroxyethyl-acetylamino, N-2-hydroxyethyl-propionylamino, N-2-hydroxypropylacetylamino, N-2-hydroxy-3-methoxypropyl-acetylamino, N-2-hydroxyethyl-methoxyacetylamino.

R may also be a polyoxyethylene group of formula: $H(OCH_2CH_2)_{2-5}-$, $Me(OCH_2CH_2)_{2-4}-$, or $Et-(OCH_2CH_2)_{2-4}-$.

Y in compounds of formula I, II and III may be: hydroxy, alkoxy or hydroxyalkoxy, as for example methoxy, ethoxy, 2-hydroxyethoxy, 2,3-dihydroxypropoxy, 1,3-dihydroxyisopropoxy, or alkylamino such as methylamino, or preferably a hydroxyalkylamino group of formula:

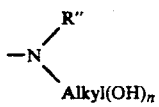

wherein R", Alkyl and n have the above mentioned meanings.

Examples of such group are the following ones: 2-hydroxyethylamino, 2-hydroxypropylamino, 2,3-dihydroxypropylamino, 1,3-dihydroxyisopropylamino, 1,3-dihydroxy-2-methyl-isopropylamino, 2,3,4-trihydroxy-1-butylamino, 1,3,4-trihydroxy-2-butylamino, 1,3-dihydroxy-2-hydroxymethyl-isopropylamino, N-methyl-N-2-hydroxyethylamino, N-methyl-N-2,3-dihydroxypropylamino, N-methyl-N-1,3-dihydroxyisopropylamino, N-2-hydroxyethyl-N-2,3-dihydroxypropylamino, N-2-hydroxyethyl-N-1,3-dihydroxyisopropylamino, N,N-bis-(2-hydroxyethyl)amino, N,N-bis-(2,3-dihydroxypropyl)amino, N,N-bis-(1,3-dihydroxyisopropyl)amino.

Z substituent in 3-position is preferably equal to —CO—Y in 1-position, but may also be a hydroxyalkylaminocarbonyl group of formula:

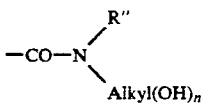

wherein R", Alkyl and n have the above mentioned meanings.

Z can also be an acylamino group, such as acetylamino, propionylamino, or a hydroxyacylamino group, such as hydroxyacetylamino, α-hydroxypropionylamino, or a N-alkyl-acylamino group, such as N-methyl-acetylamino, N-methyl-hydroxyacetylamino, or a N-hydroxyalkyl-acetylamino group, such as N-2,3-dihydroxypropyl-acetylamino, N-1,3-dihydroxyisopropyl-acetylamino, N-2-hydroxyethyl-hydroxyacetylamino, or an acylaminomethyl group, such as acetylaminomethyl or hydroxyacetylaminomethyl of formula:

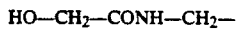

HO—CH₂—CONH—CH₂—

In the starting compounds of formula II, the substituent in the 5-position is an aminocarbonyl-alkoxy or alkylaminocarbonyl-alkoxy group, of which the following examples are reported:

| | |
|---|---|
| aminocarbonyl-methoxy | NH₂COCH₂O— |
| 1-aminocarbonyl-ethoxy | NH₂COCH(Me)O— |
| methylaminocarbonyl-methoxy | MeNHCOCH₂O— |
| 1-(methylaminocarbonyl)-ethoxy | MeNHCOCH(Me)O— |
| ethylaminocarbonyl-methoxy | EtNHCOCH₂O— |
| 1-(ethylaminocarbonyl)-ethoxy | EtNHCOCH(Me)O— |
| (2-hydroxyethylaminocarbonyl)-methoxy | HOCH₂CH₂NHCOCH₂O— |
| 1-(2-hydroxyethylaminocarbonyl)-ethoxy | HOCH₂CH₂NHCOCH(Me)O— |
| (2-methoxyethylaminocarbonyl)-methoxy | MeOCH₂CH₂NHCOCH₂O— |
| 1-(2-methoxyethylaminocarbonyl)-ethoxy | MeOCH₂CH₂NHCOCH(Me)O— |
| 1-(methylaminocarbonyl)-2-methoxy-ethoxy | MeNHCOCH(CH₂OMe)O— |
| 1-(methylaminocarbonyl)-2-ethoxy-ethoxy | MeNHCOCH(CH₂OEt)O— |
| (2,3-dihydroxypropyl-aminocarbonyl)-methoxy | HOCH₂CH(OH)CH₂NHCOCH₂O— |
| (2-hydroxy-3-methoxy-propylamino-carbonyl)-methoxy | MeOCH₂CH(OH)CH₂NHCOCH₂O— |

In the starting compounds of formula III, the substituent in 5-position is an acylamino-alkoxy group. That makes it possible to prepare a compound of formula I, in which Acyl has no hydroxy groups, in such case R necessarily carrying a hydroxy substituent. Since said hydroxy groups are desirable, because of their ability to increase water-solubility, also both Acyl and R can be substituted by said functional groups.

According to what hereinabove stated, non limitative examples of the group of formula Acyl—NH—CH₂CH(R₁)—O— in compounds of formula III, in which R₁ and Acyl are as above defined, are the following ones:

| | |
|---|---|
| 2-acetylamino-ethoxy | AcNHCH₂CH₂O— |
| 2-hydroxyacetylamino-ethoxy | HOCH₂CONHCH₂CH₂O— |
| 2-acetylamino-propoxy | AcNHCH(Me)CH₂O— |
| 2-acetylamino-1-(methoxymethyl)ethoxy | AcNHCH₂CH(CH₂OMe)O— |
| 2-α-hydroxypropionyl-aminoethoxy | HOCH(Me)CONHCH₂CH₂O— |
| 2-acetylamino-1-methyl-ethoxy | AcNHCH₂CH(Me)O— |
| 2-methoxyacetylamino-ethoxy | MeOCH₂CONHCH₂CH₂O— |
| 2-methoxyacetylamino-1-hydroxymethyl-ethoxy | MeOCH₂CONHCH₂CH(CH₂OH)O— |

According to the general definition of formula I, by means of the process of the present invention, α,ω-bis-(N-2,4,6-triiodo or tribromo-phenyl-N-α-hydroxyacylamino)alkanes of formula VI

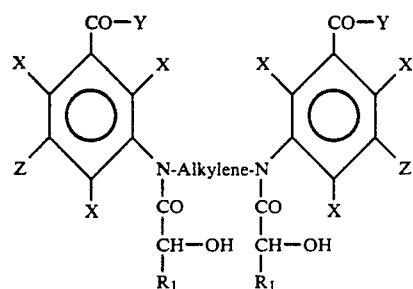

wherein:
X, Y and Z have the same meanings of formula I,
alkylene is a straight or branched $C_2-C_8$ alkylene residue, which in turn may be substituted by hydroxy groups and/or interrupted by O, S, SO or $SO_2$,
$R_1$ is H or a $C_1-C_3$ alkyl, hydroxyalkyl, alkoxyalkyl or alkoxy-hydroxyalkyl group,
can also be prepared.

The above said compounds of formula VI are obtained by a double rearrangement from the corresponding bis-(N-(2,4,6-triiodo or tribromo-phenoxyacyl)-amino)-alkanes of formula VII

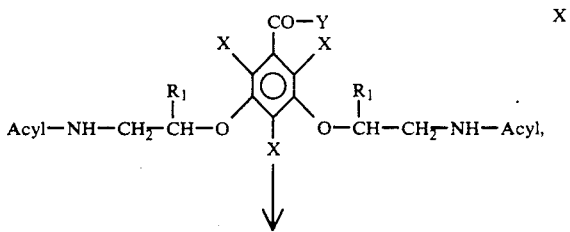

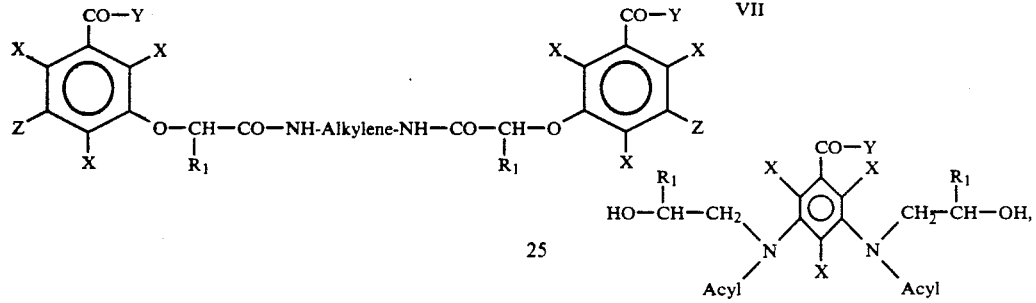

wherein Y, Z, $R_1$ and Alkylene have the same meanings as in formula VI.

From the 3,5-bis-ethers of formula VIII, by a double rearrangement, the corresponding 3,5-bis-acylamino-2,4,6-triiodo or tribromo-benzoic acid derivatives of formula IX can be prepared, according to the following scheme:

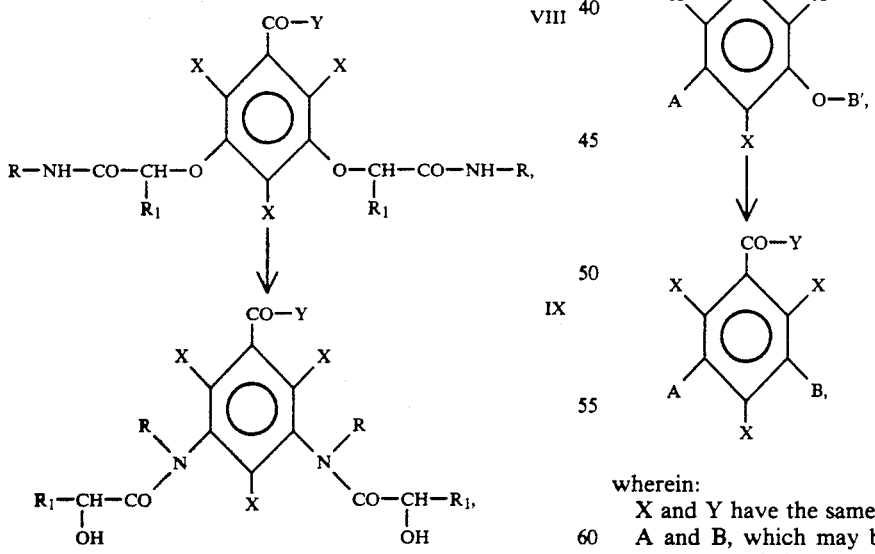

wherein X, Y, R and $R_1$ have the same meanings as in formulae I and II, respectively.

From the 3,5-bis-ethers of general formula X, by double rearrangement, the corresponding 3,5-bis-acylamino-2,4,6-triiodo or tribromo-benzoic acid derivatives of general formula XI can be prepared, according to the following scheme:

wherein X, Y, Acyl and $R_1$ have the same meanings as in formulae I, II and III, respectively.

By means of the process of the present invention, the 3,5-bis-acylamino-2,4,6-triiodo or tribromo-benzoic acid derivatives of general formula XIII, can also be prepared by rearrangement of the corresponding compounds of formula XII, according to the following scheme:

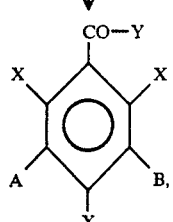

wherein:
X and Y have the same meanings as in formula I,
A and B, which may be the same or different, are groups of formula $—N(R)CO—CHOH—R_1$ or $—N(Acyl)CH_2—CHOH—R_1$ respectively defined as in formulae IX and XI,
B' is a group of formula $—CH(R_1)CONHR$ or $—CH(R_1)CH_2—$ $—NH—Acyl$ respectively defined as in formulae VIII and X.

Starting compounds necessary to carry out the synthetic process according to the invention are 5-(alkylaminocarbonyl-alkoxy)-2,4,6-triiodo or tribromobenzoic acid derivatives of formulae II or VII, 5-(acylamino-alkoxy)-2,4,6-triiodo or tribromo-benzoic acid derivatives of formula III, 3,5-bis-(alkylaminocarbonyl-alkoxy)-2,4,6-triiodo or tribromo-benzoic acid derivatives of formula VIII, 3,5-bis-(acylamino-alkoxy)-2,4,6-triodo or tribromo-benzoic acid derivatives of formula X, 3-(alkylaminocarbonylalkoxy or acylaminoalkoxy)-5-acylamino-2,4,6-triodo or tribromo-benzoic acid derivatives of formula XII.

By means of known synthetic methods, the above cited 5-hydroxy-2,4,6-triodo or tribromo-benzoic acid ether derivatives of formulae II, III, VII, VIII, X and XII are generally more easily obtainable than compounds of formula I.

The more evident advantage of this new synthetic process resides in that the above said contrast agents can be usually prepared more easily and in a shorter way, when compared to known methods.

In order to prepare non-ionic contrast agents, generally consisting in 5-hydroxyacylamino or 5-(hydroxyalkylacylamino)-2,4,6-triiodo or tribromo-bis-(hydroxy-alkyl)isophthalamides, by means of known synthetic methods, the proper intermediates are usually subjected to acylation and/or alkylation at the aromatic nitrogen in 5-position, thus obtaining the corresponding anilides and/or alkylanilides. An undesired even if partial reaction of the hydroxy groups present in the molecule with the acylating or the alkylating agent, to give the corresponding O-acetyl or O-alkyl derivatives, is in such way inevitable. This makes the purification of the final products quite difficult, or requires the use of appropriate protecting groups, in order to preserve the hydroxy groups from said side reactions. By the process of the invention, on the contrary, the use of such protecting groups is no more necessary, since acylating or alkylating agents are not used.

Synthetic schemes illustrating respectively the process of the invention (FIG. No. 1) in comparison with a known synthesis of Ioversol (FIG. No. 2, U.S. Pat. No. 4,396,598) are hereinbelow enclosed as an example.

The above said advantages of easiness and shortness of the synthesis, besides the ones deriving from avoiding the use of dangerous and polluting reactants, such as thionyl chloride, or large amounts of acetic anhydride and soda to protect and subsequently deprotect hydroxy groups, are immediately evident from a comparative examination of the two processes.

Another favourable aspect of the process resides in the remarkable easiness of the purification steps, because of the minimum amounts of salts to be removed, while, using known synthetic methods, long and expensive separation techniques are required in order to remove large amounts of such impurities.

Up to now, such rearrangement reactions of compounds of formulae II and III have never been disclosed.

Only a merely formal comparison may be done with Smiles rearrangement reaction, although remarkable differences exist even in comparison with the most similar examples of said reaction.

In this respect, see the following enclosed references:
W. E. Truce et al, Organic Reactions 18, 99–215 (1970);
J. F. Bunnet et al, Chemical Reviews 49, 362 (1951);
G. G. Wubbels et al, J. Amer. Chem. Soc. 102, 4848,4849 (1980)

E. A. Nodiff et al, J. Org. Chem. 29, 2453–2455 (1964);
G. E. Bonvicino et al, J. Org. Chem. 27, 4272–4280 (1962);
W. R. Baker, J. Org. Chem. 48, 5140–5143 (1983).

The rearrangement reaction can be carried out in water or in an organic solvent such as methanol, ethanol, isopropanol, 2-methoxyethanol, 1,2-dimethoxyethane, 1,2-propanediol, tetrahydrofuran (THF), benzene, toluene, pyridine or dimethylsulfoxide (DMSO), dimethylformamide (DMF), dimethylacetamide (DMAC) or hexamethylphosphoramide (HMPT), generally in the presence of only catalytic amounts of bases.

Alkali, such as sodium hydroxide, potassium hydroxide, lithium hydroxide, alkali metal carbonates ($Na_2CO_3$, $K_2CO_3$), alkali metal hydrogenocarbonates ($NaHCO_3$, $KHCO_3$), alkali metal borates such as borax or sodium borate, and corresponding buffer mixtures, alcoholates such as sodium ethylate, sodium methylate, potassium ethylate, potassium methylate, potassium tert-butylate, tertiary amines such as triethylamine, tributylamine, N-methyl-morpholine, N-methyl-pyrrolidine, N-methyl-piperidine, quaternary ammonium hydroxides such as tetramethylammonium hydroxide, tetraethylammonium hydroxide, tetrabutylammonium hydroxide, tetrabutylammonium flouride, benzyltrimetylammonium hydroxide, diazabicycloundecene (DBU), and tetraazacyclododecane (TAZA) can be used as bases.

Bases such as sodium amide and potassium amide, as well as alkali hydrides such as sodium hydride or potassium hydride, can also be considered as potentially useful.

Sometimes addition of crown ethers can also be useful to remarkably increase the reaction rate.

Reaction temperature may generally range from 0° to 150° C., preferably from 50° to 100° C.; it strongly depends on the kind of solvent and base used; for example, in presence of sodium hydride or, even better, of potassium hydride, the reaction proceeds in an aprotic solvent such as DMF or DMAC at a very high rate at 0° C. or even at lower temperatures.

Favourable conditions to increase reaction rate are attained carrying out the reaction in the presence of an alkali hydride in an ether, such as 1,2-dimethoxyethane, THF, or in an aprotic solvent, adding a crown ether such as 15-crown-5-(=1,4,7,10,13-pentaoxacyclopentadecane), 18-crown-6 (=1,4,7,10,13,16-hexaoxacyclooctadecane).

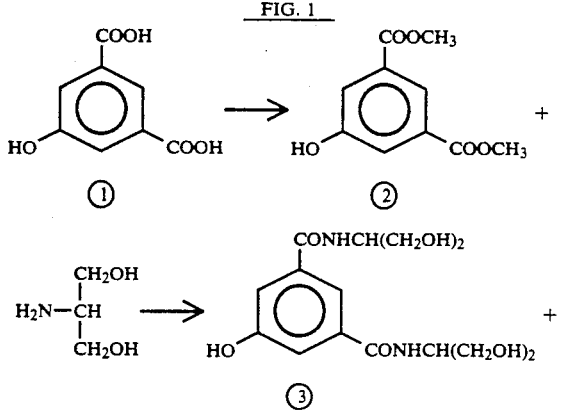

FIG. 1

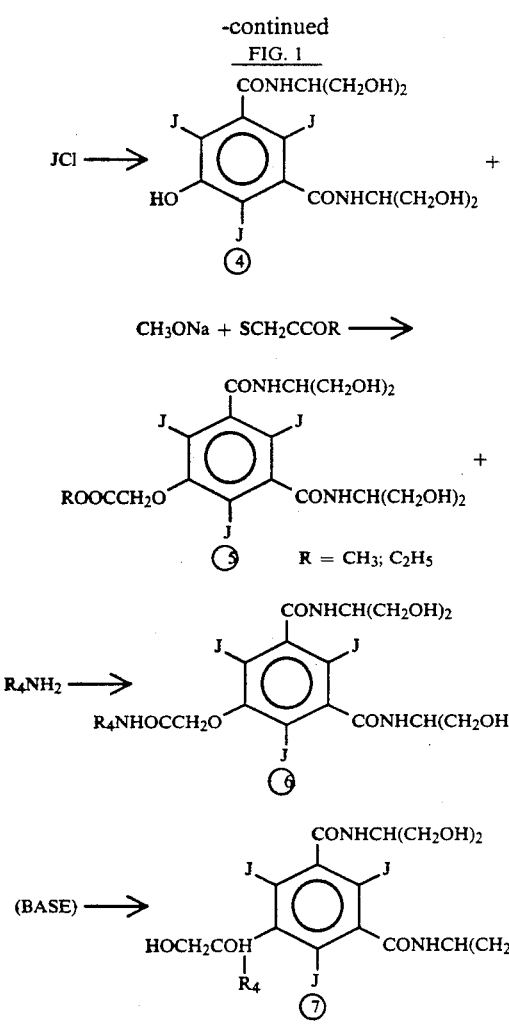
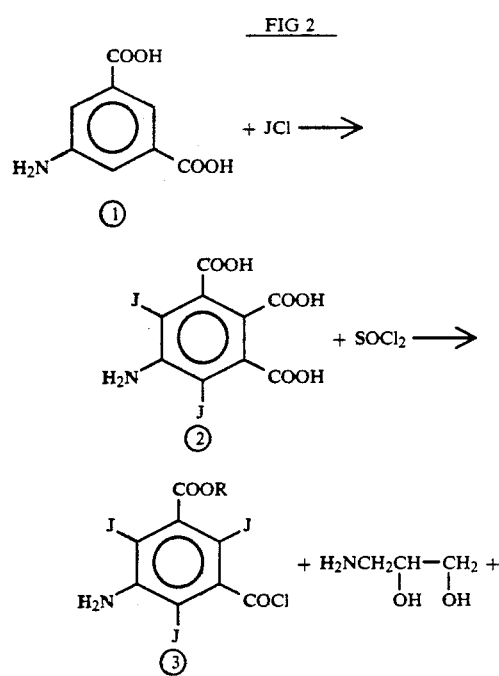
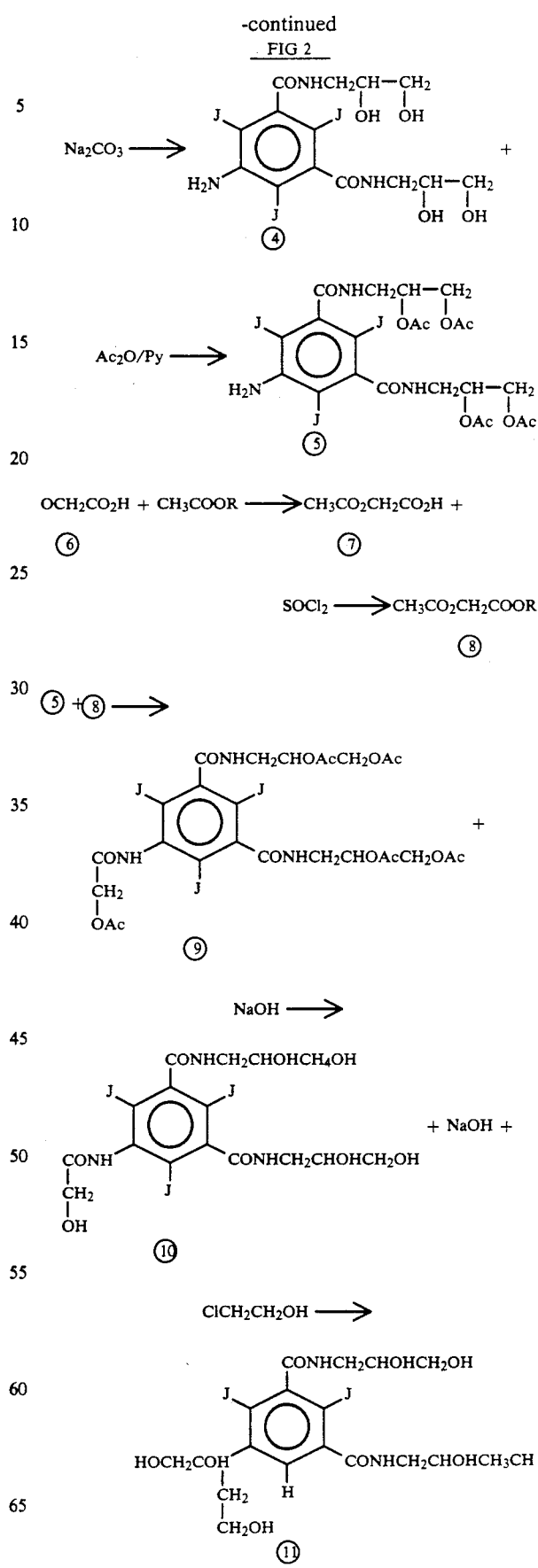

EXAMPLE 1

(S)5-[(2-hydroxypropionyl)-amino]-2,4,6-triiodo-bis-(1,3-dihydroxyisopropyl)isophthalamide. (Iopamidol).

11 g of (S) 5-(1-aminocarbonyl-ethoxy)-2,4,6-triiodo-bis-(1,3-dihydroxyisopropyl)isophtalamide (0,0141 mole) were dissolved in 110 ml of DMF. 3,6 ml of a 4M solution of $CH_3ONa$ in $CH_3OH$ (0,0144 mole) were dropped therein at room temperature. The reaction was complete after 65 hours (T.L.C. control: silica gel Merck plate $60F_{254}$/Eluent=$CHCl_3$6, $CH_3OH$3, $NH_4OH$25% 1. Developer: starch (254 nm)).

The reaction mixture was neutralized with $HCl/CH_3OH$ 4M (3.6 ml; 0,0144 mole) and, after filtration of the salts, evaporated under reduced pressure. The crude product was solidified by treatment with $CH_2Cl_2$ then, after filtration, was dissolved in water, percolated on Amberlite IR120 and Dualite A30B and eluted with water. The neutral aqueous layer was evaporated and the crude compound was crystallized from absolute ethanol.

9.5 g of (S)-5[(2-hydroxypropionyl)-amino]-2,4,6-triiodo-bis(1,3-dihydroxyisopropyl)isophthalamide (0,0122 mole) were obtained.

Yield 86.6%.

m.p. 297° C.

HPLC purity 99.4%.

$[\alpha]_{436}^{20} = -139,08°$ (c=1,25% as cupric complex): (theor.−143° C.).

Optical purity: 97.2%.

Elemental Analysis: Calc. % : C 26.28; H 2.85; I 48.99; N 5.41. Found % : C 26.27; H 2.85; I 48.91; N 5.36.

IR; $^1H$ and $^{13}C$ NMR spectra were in agreement with the proposed structure.

A) Preparation of R-5-(1-aminocarbonyl-ethoxy)-2,4,6-triiodo-bis-(1,3-dihydroxyisopropyl)isophthalamide. 35 g of R-5-(1-ethoxycarbonyl-ethoxy)-2,4,6-triiodo-bis-(1,3-dihydroxyisopropyl)isophthalamide (0.0434 mole) (Eur. Pat. Appl. 185130) were heated to 80° C. under pressure in $NH_3/CH_3OH$ 7N (0.63 mole) for 2.5 hours. Then the reaction mixture was evaporated to dryness and the resulting product was crystallized from absolute ethanol to give the desired product.

23 g of R-5-(1-aminocarbonyl-ethoxy)-2,4,6-triiodo-bis-(1,3-dihydroxyisopropyl)isophthalamide (0.0296 mole) were obtained.

Yield: 68.2%.

m.p. 110°.

HPLC purity 99.7%.

Elemental Analysis Calc. % : C 26.28; H 2.85; I 48.99; N 5.41. Found % : C 26.78; H 2.91; I 48.63; N 5.32.

IR; $^1H$ and $^{13}C$ NMR spectra were in agreement with the proposed structure.

EXAMPLE 2

S-5-[(2-hydroxypropionyl)methylamino]-2,4,6-triiodo-bis-(1,3-dihydroxyisopropyl)isophthalamide.

According to the procedure of example 1, 39 g of S-5-(1-methylaminocarbonyl-ethoxy)-2,4,6-triiodo-bis-(1,3-dihydroxyisopropyl)isophthalamide (0.0493 mole) in 390 ml of DMF were reacted with $CH_3ONa/CH_3OH$ 4M (12.3 ml; 0.0493 mole) at room temperature. When the conversion was complete (T.L.C. control: silica gel Merck plate 60 $F_{254}$/Eluent=$CHCl_3$6; $CH_3OH$ 3; $NH_4OH$ 25% 1), the reaction mixture was worked as described in example 1, to give the desired compound.

27.5 g of S-5-[(2-hydroxypropionyl)methylamino]-2,4,6-triiodo-bis-(1,3-dihydroxyisopropyl)isophthalamide (0.0347 mole) were obtained.

Yield: 70.4%; m.p. 250° C.

Analysis: Calc. % : I 48.12. Found % : I 47.99.

EXAMPLE 3

5-(N-2-hydroxyethyl-N-hydroxyacetyl-amino)-2,4,6-triiodo-bis-(2,3-dihydroxypropyl)isophthalamide (Ioversol)

17.4 g of 5-(2-hydroxyethyl)-aminocarbonylmethoxy-2,4,6-triiodo-bis-(2,3-dihydroxypropyl)isophthalamide (EP-A-0.185.130, Ex. 31) (0.0216 mole) were heated to 90° C. in 375 ml of water.

The pH of the solution was adjusted to 9 by addition of 0.05N NaOH and the reaction was monitored by T.L.C. After 5 hours, about 70–75% of the starting compound was transformed into the final product. After neutralization with 0.05N HCl, solvent was concentrated; upon cooling the major part of the unreacted starting compound crystallized and was filtered off.

The filtrate containing the title compound was made free from salts by ion-exchange resins. The final crude product was eventually purified on Amberlite XAD-2. 11.91 g of the desired compound were obtained (0.0148 mole). Yield 68%; m.p.: 195° C.; HPLC Purity: 99%. The characteristics of the obtained compound were in agreement with those of the derivative described in EP-A-0.083.964.

EXAMPLE 4

5-(N-2,3-dihydroxypropyl-N-hydroxyacetyl-amino)-2,4,6-triiodo-bis-(2,3-dihydroxypropyl)isophthalamide.

21 g of 5-(2,3-dihydroxypropyl)aminocarbonylmethoxy-2,4,6-triiodo-bis-(2,3-dihydroxypropyl)isophthalamide (EP-A-0.185.130, Ex.: 32) (0.0251 mole) were heated to 90° C. in 650 ml of water. pH was adjusted to 9 by addition of 0.05M NaOH. Disappearance of the starting compound and formation of the final one were monitored by T.L.C.

After 5 hours the reaction mixture was cooled, neutralized with 0,05M HCl and concentrated. The unreacted starting compound was crystallized off, and the filtrate was made free from salts by ion-exchange resins. The obtained crude product was purified as described in example 1.

10.1 g of the final compound (0.0121 mole) were obtained.

Yield: 48%; m.p. 195°–200°.

Elemental Analysis: Calc. % : C 27.26; H 3.13; I 45.48; N 5.02. Found % : C 26.71; H 3.26; I 45.35; N 4.88.

EXAMPLE 5

5-(N-methyl-N-hydroxyacetyl-amino)-2,4,6-triiodo-bis-(2,3-dihydroxypropyl)isophthalamide (Iomeprol)

40 g of 5-methylaminocarbonylmethoxy-2,4,6-triiodo-bis-(2,3-dihydroxypropyl)isophthalamide (EP-A-0.185. 130, Ex.: 30) (0,0515 mole) were heated to 90° C. in water and pH was adjusted to 9 by addition of 0,05M NaOH. The reaction was monitored by T.L.C. After about 4.5 hours, the reaction mixture was neutralized by means of 0.05M HCl, then the final compound was purified as described in example 1.

34.15 g of the final compound were obtained (0.0439 mole).

Yield: 85%.
m.p. 280°-282° C., with decomposition.
Elemental Analysis: Calc. % : C 26.27; H 2.85; I 48.99; N 5.41. Found % : C 26.18; H 2.87; I 48.99; N 5.39.
The product was corresponding to the one described in EP-A-0.062.281, Ex.: 9.

EXAMPLE 6

5-(N-methyl-N-hydroxyacetyl-amino)-2,4,6-triiodo-bis-(2,3-dihydroxypropyl)isophthalamide.

4 g of 5-methylaminocarbonylmethoxy-2,4,6-triiodo-bis-(2,3-dihydroxypropyl)isophthalamide (0.0051 mole) in 40 ml of DMAC were mixed at 25° C. with 1 equivalent of potassium hydride and 18-crown-6- (=1,4,7,10,13,16-hexaoxacyclooctadecane).

The reaction was monitored by T.L.C. After 1 hour, a conversion of about 75% was obtained. Solvent was evaporated under reduced pressure, then purification and recovery of the final compound were carried out according to the procedure described in example 1.

2.3 g of the final product were obtained (0.0033 mole).
Yield: 64.3%.
m.p. 280°-283° C. with decomposition.

EXAMPLE 7

1,3-bis-(N-(3,5-bis-(2,3-dihydroxypropylaminocarbonyl)-2,4,6-triiodo-phenyl)-N-hydroxyacetyl-amino)-propane 5.8 g of 1,3-bis-(3,5-bis(2,3-dihydroxypropylaminocarbonyl)-2,4,6-triiodo-phenoxyacetylamino)-propane (obtained according to the general procedure disclosed in EP-A-185.130) (0.0037 mole) were suspended in 1160 ml of 0.022M borate buffer and heated to 95° C., with constant control of pH (pH=9). A conversion of 70.22% (determined by HPLC) was obtained after about 3 hours.

Following the procedure described in example 1, the reaction mixture was then cooled to room temperature, made free from salts and purified to give the desired compound.

3.2 g of 1,3-bis-(N-(3,5-bis-(2,3-dihydroxypropylaminocarbonyl)-2,4,6-triiodo-phenyl)-N-hydroxyacetyl-amino)propane (0.002 mole), were obtained.
Yield: 54%.
m.p. 234°-236° C. with decomposition.
Analysis: Calc. % : I 48.61. Found % : I 48.23.
T.L.C. Rf=0.27 (Eluent: butanol/AcOH/H$_2$O=15:3:5).

HPLC; Rt=14 minutes; Visualizer: UV (254 nm).
Lichrosorb RP18 5/μ- (250×4).
Column Temperature: 60° C.
Eluent (gradient): A=KH$_2$PO$_4$O 0.0125M. B=CH$_3$CN/H$_2$O 1/1 v/v.
Time (min.): 0; 5; 30; 50. % B: 1; 5; 20; 75.

The general procedure followed in examples 8 to 27 to study the progress of the reaction with the change of various parameters thereof (solvent, base, temperature) is herein reported. The results are hereinbelow summarized in Table 2.

EXAMPLES 8-27

5-(N-methyl-N-hydroxyacetyl-amino)-2,4,6-triiodo-bis-(2,3-dihydroxypropyl)isophthalamide 5-methylaminocarbonylmethoxy-2,4,6-triiodo-bis-(2,3-dihydroxypropyl)isophthalamide was dissolved or suspended in the solvent in a reactor, provided with a refrigerant with a KOH valve and under nitrogen atmosphere, and the mixture was stirred at a temperature ranging from 25° C. to 95° C. The selected base, generally in an equimolecular amount to the starting product, was added to the solution (Method A) or to the suspension (Method B).

The reaction was monitored by T.L.C. or HPLC (analytical conditions are hereinbelow specified in Table 1) and conversion percentages and reaction times were evaluated and reported in table 2.

The characteristics of the obtained 5-(N-methyl-N-hydroxyacetyl-amino)-2,4,6-triiodo-bis-(2,3-dihydroxypropyl)isophthalamide were in agreement with those of the product described in EP-0.026.281, Ex.: 9.

TABLE 1

| (1) | T.L.C. conditions: |
|---|---|
| | Support = Merck silica gel plate 60 F$_{254}$ |
| | Eluent = A: chloroform 6, methanol 3, ammonia 25% 1 |
| | B: chloroform 70, methanol 30, acetic acid 2 |
| | C: 2-butanone 15, acetic acid 3, water 5 |
| | Developer = starch and exposition to UV light (254 nm). |
| (2) | H.P.L.C. conditions: |
| | Eluent (gradient) |
| | Solvent A = KH$_2$PO$_4$ 0.0125 M |
| | Solvent B = H$_2$O/CH$_3$CN 85/15 (v/v) |
| | Time (min.) 0; 5; 15; 25; |
| | % B      10; 10; 83,5; 83,5; |
| | Lichrosorb column RP-18; 5μ - (250 × 4 nm) |
| | Column T = 60° C.    Visualizer: UV (254 nm) |
| | Rt S.C.* about 12.9' |
| | Rt E.C.* about 9.5' |

*S.C. = starting compound    E.C. = end compound

TABLE 2

| Example No. | s.c. grams* | Solvent | Solvent grams | Base | Molar ratio base/s.c.* | Method | Reaction Temp. (°C.) | % of conversion | Analyt. method | Time (hrs) |
|---|---|---|---|---|---|---|---|---|---|---|
| 8 | 0,25 | Water | 50 | NaOH | 0,1 | A | 95 | 92,5 | HPLC | 5,5 |
| 9 | 0,25 | | 50 | NaOH | 1 | A | 95 | 95,2 | HPLC | 1 |
| 10 | 0,25 | | 50 | ISOSERINOL (a) | 1 | A | 95 | 93,3 | HPLC | 7 |
| 11 | 0,25 | | 50 | DBU (b) | 1 | A | 95 | 88,6 | HPLC | 1 |
| 12 | 0,25 | | 50 | TBAOH (c) | 1 | A | 95 | 90,9 | HPLC | 1 |
| 13 | 0,25 | | 50 | TAZA (d) | 1 | A | 95 | 93,8 | HPLC | 2,5 |
| 14 | 0,25 | | 50 | NH$_4$OH | 40 | A | 95 | 85,8 | HPLC | 5 |
| 15 | 0,45 | Methanol | 39,5 | NaOH/H$_2$O | 1 | B | 70 | ca 85 | TLC | 2,5 |
| 16 | 0,45 | | 39,5 | NaOH/CH$_3$OH | 1 | B | 70 | ca 85 | TLC | 3,5 |
| 17 | 0,45 | | 39,5 | CH$_3$ONa | 1 | B | 70 | ca 80 | TLC | 4,5 |
| 18 | 0,45 | | 39,5 | BzTMAOH (c) | 1 | B | 70 | ca 85 | TLC | 3,5 |
| 19 | 0,40 | 1,2 Propanedial | 50 | DBU (b) | 1 | B | 85 | 91 | HPLC | 2 |
| 20 | 0,30 | DMF | 17 | K$_2$CO$_3$ | 1 | A | 80 | 74 | HPLC | 0,25 |
| 21 | 0,50 | | 20 | DBU (b) | 1 | A | 75 | 85 | HPLC | 0,5 |

TABLE 2-continued

| Example No. | s.c. grams* | Solvent | Solvent grams | Base | Molar ratio base/s.c.* | Method | Reaction Temp. (°C.) | % of conversion | Analyt. method | Time (hrs) |
| --- | --- | --- | --- | --- | --- | --- | --- | --- | --- | --- |
| 22 | 0,50 |  | 20 | tert-BuOK | 1 | A | 75 | 68 | HPLC | 0,25 |
| 23 | 1,50 | DMAC | 18 | NaH | 1 | A | 55 | ca 40 | TLC | 0,5 |
| 24 | 0,30 |  | 19 | TBAF (f) | 1 | A | 80 | 50 | HPLC | 2 |
| 25 | 0,25 | HMPT | 67 | TAZA (d) + $CH_3ONa$ | 1 | B | 80 | ca 35 | TLC | 3,5 |
| 26 | 0,25 | (g) | 59 | $CH_3ONa$ | 1 | B | 25 | ca 50 | TLC | 2 |
| 27 | 0,25 | Pyridine | 37 | Py + $CH_3ONa$ | 1 | A | 50 | ca 50 | TLC | 0,25 |

(a) Isoserinol = 2,3-dihydroxypropylamine
(b) DBU = 1,8-Diazabicyclo[5,4,0]-7-undecene
(c) TBAOH = Tetrabutylammonium hydroxide
(d) TAZA = 1,4,7,10-Tetraazacyclododecane
(e) BzTMAOH = Benzyltrimethylammonium hydroxide
(f) TBAF = Tetrabutylammonium fluoride
(g) HMPT = Hexamethylphosphoryltriamide
*s.c. = starting compound

EXAMPLE 28

5-(N-2-hydroxyethyl-N-hydroxyacetyl-amino)-2,4,6-triiodo-bis-(2,3-dihydroxypropyl)isophthalate 7 g of 5-(N-2-hydroxyethylaminocarbonylmethoxy)-2,4,6-triiodo-bis-(2,3-dihydroxypropyl)isophthalate (obtained according to the general procedure disclosed in EP-A-185.130) were dissolved in DMF at room temperature and added with an equimolar amount of $CH_3ONa/CH_3OH$ 4M.

The reaction was monitored by T.L.C. and gave an approximate conversion percentage of 75%, after 32 hours, at room temperature.

After evaporation of the solvent, the crude compound was worked according to the method described in Example 1, to give the desired product.

4.34 g of 5-(N-2-hydroxyethyl-N-hydroxyacetyl-amino)-2,4,6-triiodo-bis-(2,3-dihydroxypropyl)isophthalate were obtained.

Yield: 62%.

Elemental analysis: Calc. % : C 26.7; H 2.7; I 47.09; N 1.7. Found % : C 26.2; H 3.0; I 46.95; N 2.01.

By the same procedure, 5-(N-methyl-N-hydroxyacetyl-amino)-2,4,6-triiodo-bis-(2,3-dihydroxypropyl)isophthalate was obtained from 5-(N-methylaminocarbonylmethoxy)-2,4,6-triiodo-bis-(2,3-dihydroxypropyl)isophthalate (obtained according to the general procedure illustrated in EP-A-185.130).

Yield: 70%.

m.p.: 104°-110° C.

Elemental analysis: Calc. % : C 26,21; H 2.59; I 48.87; N 1.80. Found % : C 25.10; H 2.64; I 47.40; N 2.02; $H_2O$ 1.2.

EXAMPLE 29

5-(N-1,3-dihydroxyisopropyl-N-hydroxyacetyl-amino)-2,4,6-tribromo-bis-(1,3-dihydroxyisopropyl)isophthalamide.

8.7 g of 5-(1,3-dihydroxyisopropylaminocarbonyl)-methoxy-2,4,6-tribromo-bis-(1,3-dihydroxyisopropyl)isophthalamide (EP-A-185.130; Ex. 12) were suspended in 0.025M borate buffer (pH=9) and heated to 95° C., keeping constant pH. Rearrangement was monitored by NMR (following the decrease of the signal of the aromatic C in the 5-position bound to the oxygen and the rise of the signal of the aromatic C in 5-position bound to the nitrogen atom, each of them respectively characterizing the starting and the final compound). The reaction was complete in about 18 hours, then the reaction mixture was treated according to the method described in Ex. 1, to give the desired compound. 4.26 g of 5-(N-1,3-dihydroxyisopropyl-N-hydroxyacetyl-amino)-2,4,6-tribromo-bis-(1,3-dihydroxyisopropyl)isophthalamide were obtained.

Yield: 49%.

Analysis: Calc. % : Br 34.43. Found % : Br 34.28.

$^{13}C$ NMR (Bruker AC200, provided with ASPECT 3000). Spectra were recorded in DMSO at room temperature.

Chemical shifts of aromatic C in 5-position (referred to TMS): $C_5$ bound to —OR = 154.9 ppm (starting compound). $C_5$ bound to —N< = 147 ppm (final compound).

EXAMPLE 30

5-(N-methyl-N-hydroxyacetyl-amino)-2,4,6-triiodo-((N-2,3-dihydroxypropyl)-(N'-2-hydroxyethyl))isophthalamide 7,47 g of 5-(methylaminocarbonyl-methoxy)-2,4,6-triiodo-((N-2,3-dihydroxypropyl)-(N'-2-hydroxyethyl))isophthalamide (obtained according to the general procedure disclosed in EP-A-185.130) (0,01 mole) were suspended in 75 ml of water and heated to 95° C. 15 ml of NaOH 0,05M were added and the reaction was stirred for 1 hour. Then, after cooling, the mixture was filtered and purified on Amberlite IR 120 (1,5 ml) and Amberlite IRA 400 (3 ml).

The eluate was evaporated and the crude residue was crystallized from absolute ethanol.

5,1 g of 5-(methyl-N-hydroxyacetyl-amino)-2,4,6-triiodo((N-2,3-dihydroxypropyl)-(N'-2-hydroxyethyl)-)isophthalamide were obtained.

Yield: 68.3%.

mp: 259° C.

HPLC purity: 93%.

IR; $^1H$ and $^{13}C$ NMR spectra were in agreement with the proposed structure.

EXAMPLE 31

1,3-bis-(N-3,5-bis-(1,3-dihydroxyisopropylaminocarbonyl)-2,4,6-triiodo-phenyl)-N-hydroxyacetyl-amino)-2-hydroxy-propane 2,5 g of 1,3-bis(3,5-bis-(1,3-dihydroxyisopropylaminocarbonyl)-2,4,6-triiodo-phenoxy-acetylamino)-2-hydroxy-propane (obtained according to the general procedure disclosed in EP-A-185.130) (0,00158 mole) were suspended into 50 ml of water containing NaOH (0.0032 mole) and heated to 80° C.

The reaction was monitored by H.P.L.C.; after 3.5 hours a conversion of 80% was obtained. After cooling and neutralization, the reaction mixture was worked according to the usual way of Example 1 and the final compound was purified by preparative HPLC.

Preparative purification conditions:
Column: HIBAR lichrosorb RP-8; 7μ (250×10).
Eluent: A=H₂O. B=H₂O/CH₃CN 1/1 v/v.
Gradient: (flow: 6 ml/min.); Visualizer=254 nm.
T(min): 0.0; 8.0; 12.0; 28.0; 35.0; %B; 10; 18; 18; 90; 90.

1,1 g of 1,3-bis-(N-(3,5-bis-(1,3-dihydroxyisopropylaminocarbonyl)-2,4,6-triiodo-phenyl)-N-hydroxyacetyl-amino)-2-hydroxy-propane were obtained.
Yield: 44%.
m.p. 216°-222° C.
NMR; ¹³C (Bruker AC200, provided with ASPECT 3000). Spectra were recorded in DMSO at room temperature.

A: (starting compound)

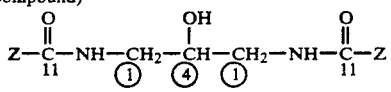

wherein: Z =

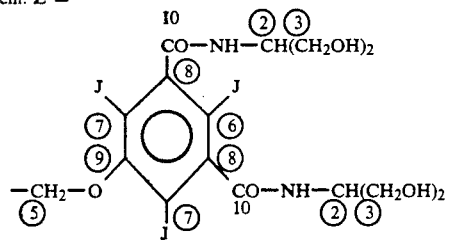

B: (final compound)

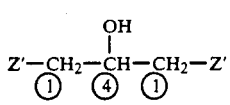

wherein: Z' =

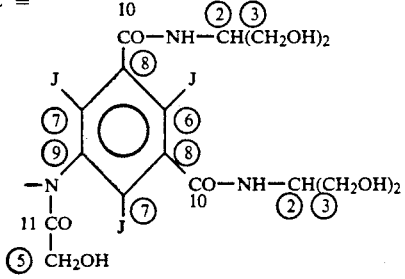

| A | | B |
|---|---|---|
| 42,24 | ① | 43,91 |
| 53,05 | ② | 53,10 |
| 69,30 | ③ | 59,42 |
| 68,16 | ④ | 70,15 |
| 70,19 | ⑤ | 71,78 |
| 87,31 | ⑥ | 82,78 |
| 90,37 | ⑦ | 92,40 |
| 150,46 | ⑧ | 151,42 |
| 156,63 | ⑨ | 145,31 |
| 166,54 | 10 | 169,07 |
| 168,70 | 11 | 172,04 |

Chemical shifts are expressed in ppm referred to TMS.

HPLC; Rt=9.65; 10.10 minutes (isomeric mixture).
Lichrosorb RP-8 column; 5μ (250×4).
Eluent: A=H₂O. B=H₂O/CH₃CN 1/1 v/v.
Gradient: (flow: 1 ml/min).
Visualizer: UV (254 nm).
T (min.)=0.0; 8.5; 12.0; 23.0; 35.0; %B=10; 20; 20; 90; 90.

EXAMPLE 32

1,3-bis-(N-(3,5-bis-(N,N-bis-(2-hydroxyethyl)aminocarbonyl)-2,4,6-triiodo-phenyl)-N-hydroxyacetyl-amino)-2,2-bis-(hydroxymethyl)-propane A) 1,3-bis-(chloroacetylamino)-2,2-bis-(hydroxymethyl)-propane 6.7 g of 2,2-bis-(aminomethyl)-propane-1,3-diol (obtained by a full conventional way; see: Beilstein 4 E III page 850; E IV page 1883) (0.05 mole) in 25 ml of methanol were dropped into a solution of 12 g of methylchloroacetate (0.11 mole) in 35 ml of methanol, while the temperature was kept between 0° and 5° C. Then the temperature was allowed to raise to 20°-25° C. and the mixture was stirred for 20 hours, until pH became neutral.

Solvent was then evaporated and the residue was solidified under vacuum and in presence of P₂O₅.

The crude residue was boiled three times with chloroform (3×40 ml) and the total organic layer was filtered and evaporated to give the desired product. 8,4 g of 1,3-bis-(chloroacetylamino)-2,2-bis-(hydroxymethyl)-propane were obtained.
Yield: 58.6%.
Elemental analysis: Calc. %: C 37.64; H 5.62; Cl 24.69. Found %: C 37.33; H 5.67; Cl 24.40.

B) 1,3-bis-(3,5-bis-(N,N-bis-(2-hydroxyethyl)aminocarbonyl)-2,4,6-triiodo-phenoxy-acetylamino)-2,2-bis-(hydroxymethyl)-propane 2.3 g of 1,3-bis-(chloroacetylamino)-2,2-bis-(hydroxymethyl)-propane (0.008 mole) and 2.4 g of sodium iodide (0.016 mole) were dissolved in 20 ml of water and heated to 40° C. To the mixture was dropwise added a solution of 11.74 g of 5-hydroxy-2,4,6-triiodo-bis-(N,N-bis-(2-hydroxyethyl))-isophthalamide (obtained according to the general procedure disclosed in EP-A-185.130) (0.016 mole) in 32 ml of NaOH 0.5M (0.016 mole), then the resulting solution was heated to 80° C. for 24 hours.

After cooling, the solution was diluted to 250 ml with water, percolated on Amberlite IRA 400 (60 ml) and Amberlite IR 120 (30 ml) and eluted with water. The aqueous layer was evaporated to give the desired product.

8.1 g of crude 1,3-bis-(3,5-bis-(N,N-bis-(2-hydroxyethyl)aminocarbonyl)-2,4,6-triiodo-phenoxyacetylamino)-2,2-bis-(hydroxymethyl)-propane were obtained.
Yield: 60.2%.
mp: 198° C.
Elemental Analysis: Calc. %: C 29.27; H 3.35; I 45.27; N 4.99. Found %: C 28.74; H 3.39; I 43.20; N 4.91.

IR; ¹H and ¹³C NMR spectra were in agreement with the proposed structure.

C) 1,3-bis-(N-3,5-bis-(N,N-bis-(2-hydroxyethyl)aminocarbonyl-2,4,6-triiodo-phenyl)-N-hydroxyacetyl-amino)-2,2-bis-(hydroxymethyl)-propane 3.36 g of 1,3-bis-(3,5-bis-(N,N-bis-(2-hydroxyethyl)aminocarbonyl)-2,4-6-triiodo-phenoxy-acetylamino)-2,2-bis-(hydroxymethyl)-propane (0.002 mole) were suspended into 65 ml of water containing NaOH (0.004 mole) and heated to 85° C. Percentage of conversion was monitored by HPLC. When a conversion of 85% was obtained, the mixture was cooled and worked according to the usual way of example 1 and the desired product was purified by preparative HPLC.

Preparative purification condition:
Column: HIBAR lichrosorb RP-8; 7μ (250×10).
Eluent: A=H₂O. B=H₂O/CH₃CN 1/1 v/v.
Gradient: (flow: 6 ml/min); Visualizer: UV (245 nm).
T (min): 0.0; 8.0; 12.0; 28.0; 35.0; %B: 10; 18; 18; 90; 90.

1 g of 1,3-bis-(N-3,5-bis-(N,N-bis-(2-hydroxyethyl-)aminocarbonyl)-2,4,6-triiodo-phenyl)-N-hydroxyacetyl-amino)-2,2-bis-(hydroxymethyl)-propane was obtained.

Yield: 29.8%.

IR; ¹H and ¹³C NMR spectra were in agreement with the proposed structure.

By the same procedure, 1,3-bis-(chloroacetylamino)-2,2-bis-(hydroxymethyl)-propane was reacted with 5-hydroxy-2,4,6-triiodo-((N-2,3-dihydroxypropyl)-(N'-2-hydroxyethyl))isophthalamide (obtained according to the general procedure disclosed in EP-A-185.130) to give the corresponding 1,3-bis-(3-(2,3-dihydroxy-propylaminocarbonyl)-5-(2-hydroxyethylaminocarbonyl)-2,4,6-triiodo-phenoxyacetylamino)-2,2-bis-(hydroxymethyl)-propane, which in turn was rearranged to give the corresponding 1,3-bis-(N-(3-(2,3-dihydroxy-propylaminocarbonyl)-5-(2-hydroxyethylaminocarbonyl)-2,4,6-triiodo-phenyl)-N-hydroxyacetyl-amino)-2,2-bis-(hydroxymethyl)-propane.

IR; ¹H and ¹³C NMR spectra were in agreement with the proposed structure.

By the same procedure, 1,3-bis-(chloroacetylamino)-2,2-bis-(hydroxymethyl)-propane was reacted with 5-hydroxy-2,4,6-triiodo-((N-1,3-dihydroxyisopropyl)-(N'-2-hydroxyethyl))-isophthalamide (obtained according to the general procedure disclosed in EP-A-185.130) to give the corresponding 1,3-bis-(3-(1,3-dihydroxyiso-propylaminocarbonyl)-5-(2-hydroxyethylaminocarbonyl)-2,4,6-triiodo-phenoxyacetylamino)-2,2-bis-(hydroxymethyl)-propane, which in turn was rearranged to give the corresponding 1,3-bis-(N-(3-(1,3-dihydroxyiso-propylaminocarbonyl)-5-(2-hydroxyethylaminocarbonyl)-2,4,6-triiodo-phenyl)-N-hydroxyacetyl-amino)-2,2-bis-(hydroxymethyl)-propane.

IR; ¹H and ¹³C NMR spectra were in agreement with the proposed structure.

EXAMPLE 33

3,5-bis-(N-2-hydroxyethyl-N-hydroxyacetyl-amino)-2,4,6-triiodo-(1,3-dihydroxyisopropyl)benzamide 3,2 g of 3-(N-2-hydroxyethyl-N-hydroxyacyl-amino)-5-(N-2-hydroxyethylaminocarbonylmethoxy)-2,4,6-triiodo-(1,3-dihydroxyisopropyl)benzamide were suspended in DMF and added with CH₃ONa/CH₃OH up to pH=9. The reaction was kept at room temperature for 48 hours, then it was worked according to the usual procedure of example 1 to give the desired compound.

1,54 g of 3,5-bis-(N-2-hydroxyethyl-N-hydroxyacetyl-amino)-2,4,6-triiodo-(1,3-dihydroxyisopropyl)benzamide were obtained.

Yield: 48.1%.

Elemental analysis: Calc. %: C 26.76; H 2.97; I 47.21; N 5.20. Found %: C 26.32; H 2.89; I 47.31; N 5.20.

What is claimed is:

1. A process for the preparation of 5-acylamino-2,4,6-triiodo or tribromo-benzoic acid derivatives of formula I

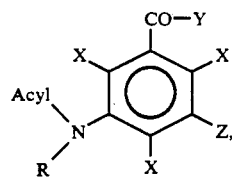

wherein:
X is I or Br, with the proviso that they are all the same;
Acyl is a C₂-C₆ hydroxyalkanoyl, alkoxyalkanoyl or alkoxy-hydroxyalkanoyl group or a C₂-C₄ unsubstituted alkanoyl group,
R is H or a C₁-C₆ alkyl, hydroxyalkyl, alkoxyalkyl or alkoxy-hydroxyalkyl group, or a H(OCH₂CH₂-)₂₋₅—, Me(OCH₂CH₂)₂₋₄— or Et(OCH₂CH₂)₂₋₄— group, or a group of formula

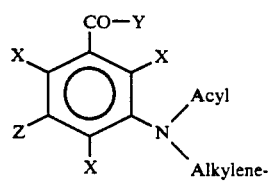

wherein X, Y, Z and Acyl have respectively the same meanings as in formula I and Alkylene- is a straight or branched C₂-C₈ alkylene group, which is unsubstituted or substituted by hydroxy groups and/or interrupted by O,S, SO or SO₂,
Y is a hydroxy, alkoxy, hydroxyalkoxy, alkylamino group or a hydroxyalkylamino group of formula

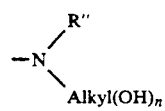

wherein R" is H or a C₁-C₅ alkyl, hydroxyalkyl, alkoxyalkyl or alkoxy-hydroxyalkyl group, Alkyl is a C₂-C₅ straight or branched alkyl group and n=1, 2 or 3,
Z has the same meaning of CO—Y in formula I or is a hydroxyalkylaminocarbonyl group of formula

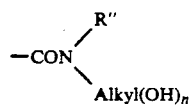

wherein R", Alkyl and n are as above defined or Z is a C₂-C₅ acylamino, hydroxyacylamino, N-alkylacylamino, N-hydroxyalkylacylamino or acylaminomethyl group, with the proviso that at least one of the two Acyl or R groups is hydroxy substituted,
said process being characterized in that 5-(alkylaminocarbonyl-alkoxy)-2,4,6-triiodo or tribromobenzoic acid derivatives of formula II, or 5-(acylamino-alkoxy)-2,4,6-triiodo or tribromo-benzoic acid derivatives of formula III

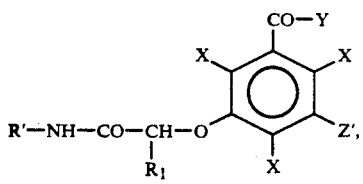

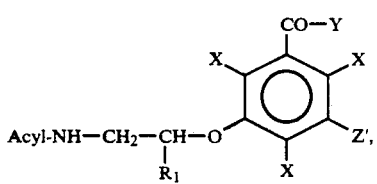

wherein:

X and Y have the same meanings as in formula I,

Z' is a) the same as Z in formula I, b) a group of formula

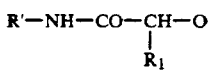

or c)

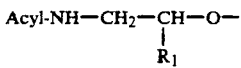

wherein R', R₁ and Acyl are as hereinbelow defined, R' is a), H; b) a $C_1$–$C_6$ alkyl, hydroxyalkyl, alkoxyalkyl or alkoxy-hydroxyalkyl group; c) a $H(OCH_2CH_2)_{2-5}$—, $Me(OCH_2CH_2)_{2-4}$— or et-$(OCH_2CH_2)_{2-4}$— group, or d) a group of formula

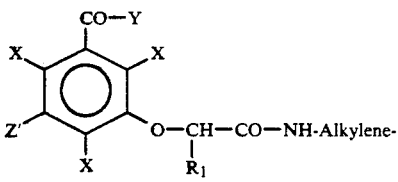

wherein X, Y, Z' are as above defined, R₁ is as hereinbelow defined, Alkylene- is a straight or branched $C_2$–$C_8$ alkylene group, which is unsubstituted or substituted by hydroxy groups and/or interrupted by O, S, SO or $SO_2$, R₁ is H or a $C_1$–$C_3$ alkyl, hydroxyalkyl or alkoxyalkyl group, Acyl is a a) $C_2$–$C_6$ hydroxyalkanoyl, b) alkoxyalkanoyl c) alkoxy-hydroxyalkanoyl group or an unsubstituted $C_2$–$C_4$ alkanoyl group, are subjected, to a rearrangement reaction to give the desired compounds of formula I in the presence of a base in an aqueous medium, said base being sodium hydroxide, lithium hydroxide, potassium hydroxide, an alkali metal carbonate or alkali metal bicarbonate, an alkali metal borate, a tertiary amine or a quaternary ammonium hydroxide.

2. A process according to claim 1, wherein the rearrangement reaction is carried out at a temperature ranging from 20° C. to 150° C., preferably from 50° C. to 100° C.

3. A process according to claim 1, wherein the rearrangement reaction is carried out in water or in a water-alcohol mixture, at a pH value ranging from 8 to 11.

4. A process according to claim 1 for the preparation of 5-acylamino-2,4,6-triiodo or tribromo-benzoic acid derivatives of formula I

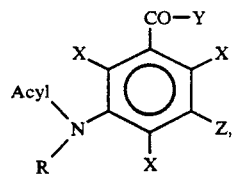

wherein:

X, Y, Z and Acyl are defined according to claim 1,

R is a $C_2$–$C_5$ 2-hydroxyalkyl or alkoxy-2-hydroxyalkyl group.

5. A process according to claim 1 for the preparation of 5-(N-alkyl-N-hydroxyacyl-amino)-2,4,6-triiodo or tribromo-bis-(hydroxyalkyl)-isophthalamides of formula IV

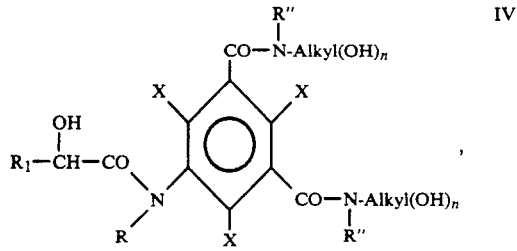

wherein:

X, R₁ and —N(R")Alkyl(OH)ₙ are defined according to claim 1

R is a $C_1$–$C_5$ Z hydroxyalkyl or alkoxy-2-hydroxyalkyl group, in which process 5-(alkylaminocarbonyl-alkoxy)-2,4,6-triiodo or tribromo-bis-(hydroxyalkyl)isophthalamides of formula II are subjected to a rearrangement reaction, to give the desired compounds of formula IV.

6. A process according to claim 1 for the preparation of 5-(N-hydroxyalkyl-N-acyl-amino)-2,4,6-triiodo or tribromo-bis-(hydroxyalkyl)isophthalamides of formula V

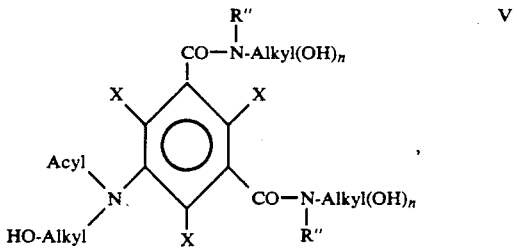

wherein:

X, Acyl and —N(R")—Alkyl(OH)ₙ are defined according to claim 1,

OH—Alkyl— is a $C_1$–$C_5$ 2-hydroxyalkyl or alkoxy-2-hydroxyalkyl group in which process 5-(acylamino-alkoxy)-2,4,6-triiodo or tribromo-bis-(hydroxyalkyl)isophthalamides of formula III, are subjected to a rearrangement reaction, to give the desired compounds of formula V.

7. A process according to claim 1 for the preparation of α,ω-bis-(N-3,5-bis-(hydroxy-alkylaminocarbonyl)-2,4,6-triiodo or tribromo-phenyl)-N-acyl-amino)-alkanes or hydroxyalkanes of formula VI

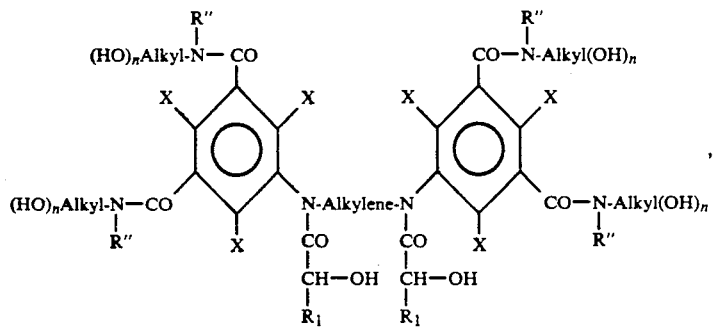

VI wherein:
X, $R_1$, N(R'')—Alkyl(OH)$_n$ and Alkylene— are defined according to claim 1,
in which process α,ω-bis-(3,5-bis-(hydroxyalkylaminocarbonyl)-2,4,6-triiodo or tribromo-phenoxyacylamino)-alkanes of formula VII

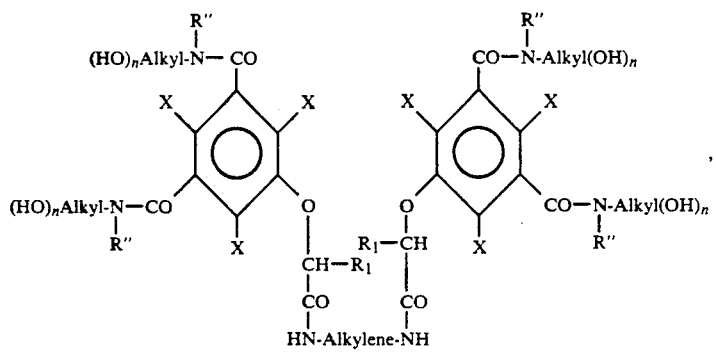

VII wherein:
X, $R_1$, N(R'')—Alkyl(OH)$_n$ and Alkylene— are defined according to claim 1, are subjected to a double rearrangement reaction, to give the desired compounds of formula VI.

8. A process according to claim 1 for the preparation of 3,5-bis-(N-alkyl-N-acylamino)-2,4,6-triiodo or tribromo-benzoic acid derivatives of formula IX, by means of a double rearrangement reaction of corresponding 3,5-bis-(alkylaminocarbonyl-alkoxy)-2,4,6-triiodo or tribromo-benzoic acid derivatives of formula VIII, according to the following scheme:

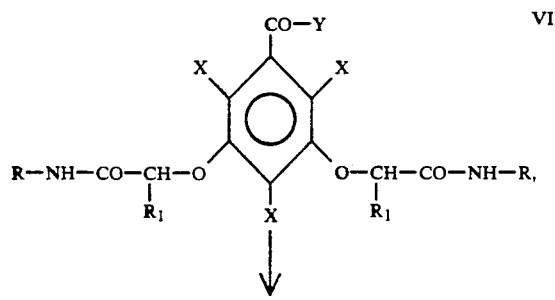

VIII

-continued

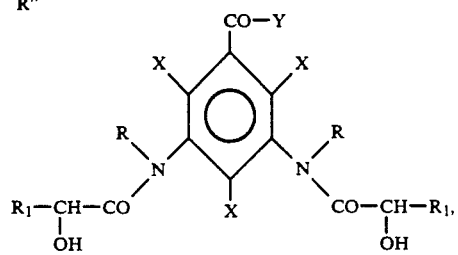

IX wherein:
X, Y and $R_1$ are defined according to formulae I and II in claim 1,
R is a $C_1$-$C_5$ Z hydroxyalkyl or alkoxy-2-hydroxyalkyl group.

9. A process according to claim 1 for the preparation of 3,5-(N-alkyl-N-acylamino)-2,4,6-triiodo or tribromo-benzoic acid derivatives of formula XI, by means of a double rearrangement reaction of corresponding 3,5-bis-(acylamino-alkoxy)-2,4,6-triiodo or tribromo-benzoic acid derivatives of formula X according to the following scheme:

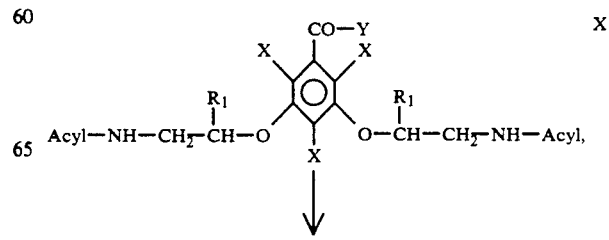

X

-continued

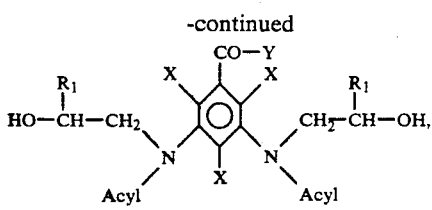

wherein:

X, Y, R₁ and Acyl are defined according to formulae I III in claim 1.

10. A process for the preparation of 3-(N-alkyl-N-acylamino)-5-(N-alkyl-N-acylamino)-2,4,6-triiodo or tribromo-benzoic acid derivatives of formula XIII, by means of a rearrangement reaction of corresponding 3-(N-alkyl-N-acylamino)-5-alkoxy-2,4,6-triiodo or tribromo benzoic acid derivatives of formula XII, according to the following scheme:

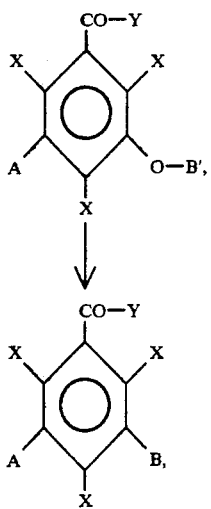

wherein:

X is I or Br with the proviso that they are the same;
Y is a hydroxy, alkoxy, hydroxyalkoxy, alkylamino group or hydroxylalkylamino group of formula

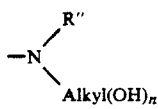

wherein R" is H or a C₁-C₅ alkyl, hydroxyalkyl, alkoxyalkyl or alkoxy-hydroxyalkyl group, Alkyl is a C₂-C₅ straight or branched alkyl group and n=1, 2 or 3, A and B which are the same or different, are groups of formula —N(R)COCHOH—R₁ or —N-(Acyl)CH₂CHOH—R₁ defined as in claim 9, B' is a group of formula —CH(CR₁)CONHR or —CH(R₁)CH₂—NH—Acyl defined as in claim 9, said rearrangement being carried out in the presence of a base in an aqueous medium, said base being sodium hydroxide, lithium hydroxide, potassium hydroxide, an alkali metal carbonate or alkali metal bicarbonate, an alkali metal borate, a tertiary amine or a quaternary ammonium hydroxide.

11. A process according to claim 1 wherein said derivative of said 5-acylamino-2,4,6-triiodo or 2,4,6-tribromo-benzoic acid is a member selected from the group consisting of:

N,N'-bis[2-hydroxy-1-(hydroxymethyl)-ethyl]-5-[(2-hydroxy-1-oxopropyl)amino]-2,4,6-triiodo-1,3-benzenedicarboxyamide;

N,N'-bis(2,3-dihydroxypropyl)-5-[(hydroxy-acetyl)methylamino]-2,4,6-triiodo-1,3-benzenedicarboxyamide;

N,N'-bis(2,3-dihydroxypropyl)-5-[(hydroxyacetyl)(2-hydroxyethyl)amino]-2,4,6-triiodo-1,3-benzenedicarboxyamide;

N,N'-bis[2-hydroxy-1-(hydroxymethyl)ethyl]-5-[2-hydroxy-1-oxopropyl)methylamino]-2,4,6-triiodo-1,3-benzenedicarboxyamide;

N,N'-bis[2-hydroxy-1-(hydroxymethyl)ethyl]-5-[(hydroxyacetyl)methylamino]-2,4,6-triiodo-1,3-benzenedicarboxyamide;

1,3-bis[N-(3,5-bis-(2,3-dihydroxypropylaminocarbonyl)-2,4,6-triiodo-phenyl)-N-hydroxyacetylamino]propane;

1,4-bis[N-(3,5-bis-(1,3-dihydroxyisopropylaminocarbonyl)-2,4,6-triiodo-phenyl)-N-hydroxyacetylamino]2,3-dihydroxybutane.

12. A process for the preparation of a 3-(N-alkyl-N-acylamino)-5-(N-alkyl-N-acylamino)-2, triiodo or tribromo-benzoic acid derivative of formula XIII, by means of a rearrangement reaction of 3-(N-alkyl-N-acylamino)-5-alkoxy-2,4,6-iodo or tribromo benzoic acid derivative of formula XII according to the following scheme:

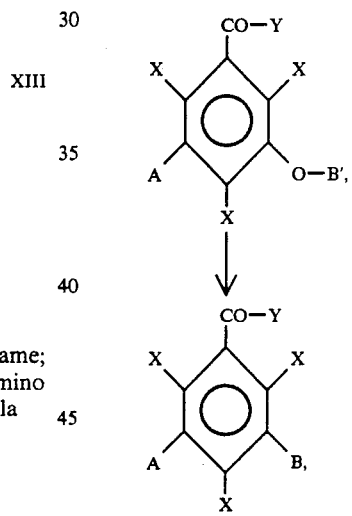

wherein X is I or Br with the proviso that they are the same; Y is a hydroxy, alkoxy, hydroxyalkoxy, alkylamino group or a hydroxyalkylamino group of formula

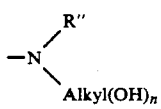

wherein R" is H or a C₁-C₅ alkyl, hydroxyalkyl, alkoxyalkyl or alkoxy-hydroxyalkyl group, alkyl is a C₂-C₅ straight or branched alkyl group and n=1, 2 or 3, A and B which are the same or different, are groups of formula —N(R)COCHOH—R₁ or —N-(Acyl)CH₂CHOH—R₁ defined as in claim 8;

B' is a group of formula —CH(R₁)CONHR or —CH(R₁)CH₂—NH—Acyl defined as in claim 8.

* * * * *